(12) United States Patent
Funk et al.

(10) Patent No.: US 9,057,666 B2
(45) Date of Patent: Jun. 16, 2015

(54) METHOD OF AND APPARATUS FOR MEASURING VISCOUS AND ELASTIC PROPERTIES OF A GLUTEN-CONTAINING SUBSTANCE

(75) Inventors: Robert C. Funk, Auburn, IL (US); Bo Allvin, Vendelso (SE); Jan Perten, Djursholm (SE)

(73) Assignee: PERTEN INSTRUMENTS INC., Springfield, IL (US)

( * ) Notice: Subject to any disclaimer, the term of this patent is extended or adjusted under 35 U.S.C. 154(b) by 1227 days.

(21) Appl. No.: 12/996,164

(22) PCT Filed: Jun. 4, 2008

(86) PCT No.: PCT/SE2008/050660
§ 371 (c)(1),
(2), (4) Date: Feb. 3, 2011

(87) PCT Pub. No.: WO2009/148369
PCT Pub. Date: Dec. 10, 2009

(65) Prior Publication Data
US 2011/0171354 A1    Jul. 14, 2011

(51) Int. Cl.
*G01N 3/06*    (2006.01)
(52) U.S. Cl.
CPC .......... *G01N 3/06* (2013.01); *G01N 2203/0089* (2013.01); *G01N 2203/0094* (2013.01)
(58) Field of Classification Search
CPC ...................................................... G01N 33/10
USPC ........ 426/231; 99/486; 73/760, 781–790, 796
See application file for complete search history.

(56) References Cited

U.S. PATENT DOCUMENTS 4,868,769 A * 9/1989 Persson .......................... 702/30
5,177,997 A * 1/1993 Maciejewski ................ 73/54.24
(Continued)

FOREIGN PATENT DOCUMENTS

| DE | 3011377 A1 | 10/1981 |
| FR | 2114204 A | 6/1972 |
| GB | 1013717 A | 12/1965 |

(Continued)

OTHER PUBLICATIONS

International Search Report, dated Feb. 6, 2009, from corresponding PCT application.

*Primary Examiner* — Steven Leff
(74) *Attorney, Agent, or Firm* — Young & Thompson (57) ABSTRACT

A method of measuring viscous and elastic properties of a gluten-containing substance includes: bringing the gluten-containing substance into a powder, adding a predetermined amount of aqueous liquid to a predetermined amount of the powder, kneading the powder and liquid to a dough to develop the viscoelastic character of the gluten in the dough- and extracting viscoelastic gluten from the dough by rinsing with the liquid. The method further includes:
shaping the gluten,
placing the shaped gluten between two parallel planar surfaces,
compressing the gluten by moving the planar surfaces towards each other at a controlled rate, until a maximum compression force or a minimum spacing is reached,
releasing the force on the planar surfaces so that these can move away from each other due to elastic recovery of the compressed gluten,
measuring the distance between the planar surfaces during the compression and elastic recovery of the gluten, and
storing the measured values.

20 Claims, 6 Drawing Sheets

(56) References Cited

U.S. PATENT DOCUMENTS

| | | | |
|---|---|---|---|
| 5,277,058 A * | 1/1994 | Kalyon et al. | 73/54.11 |
| 2002/0178796 A1 | 12/2002 | Barbe et al. | |
| 2004/0149044 A1 | 8/2004 | Kushwaha et al. | |

FOREIGN PATENT DOCUMENTS

| | | |
|---|---|---|
| GB | 2326723 A | 12/1998 |
| SU | 432386 A | 11/1974 |
| WO | 0144785 A1 | 6/2001 |

* cited by examiner

METHOD OF AND APPARATUS FOR MEASURING VISCOUS AND ELASTIC PROPERTIES OF A GLUTEN-CONTAINING SUBSTANCE

TECHNICAL FIELD

The present invention relates to a method of measuring viscous and elastic properties of a gluten-containing substance including the steps of bringing the gluten-containing substance e.g. wheat, into a powder e.g. a whole meal or flour, adding a predetermined amount of aqueous liquid e.g. saline water, to a predetermined amount of said powder, kneading said powder and liquid to a dough—i.e. adding kinetic energy to obtain a dough and to develop the viscoelastic character of the gluten in the dough—and extracting viscoelastic gluten from the dough by rinsing with said liquid, and an apparatus for performing this method.

BACKGROUND OF THE INVENTION

Among the cereal flours, wheat flour has the ability to form a strong, cohesive dough that retains gas and produces a light, aerated baked product. Wheat proteins, and more specifically the gluten proteins, are believed to be primarily responsible for that uniqueness of wheat. When wheat flour is mixed with water, a cohesive, viscoelastic dough is formed. The viscous part is sometimes referred to as plastic viscosity or plasticity. No other cereal flour forms a dough with a similar viscoelastic character. Furthermore, it is generally established that the gluten proteins govern the bread-making quality of the various wheat flours. Flours milled from different wheat cultivars vary widely in their loaf volume potential. Even at constant protein content and using the same baking process, it has been shown that a large variation in loaf volume can still exist. Thus, the quality of the protein in wheat can vary. The quality characteristics of protein are often referred to as functional properties and gluten strength (*R. Carl Hoseney, Principles of Cereal Science and Technology, 2$^{nd}$ Ed*, 1994, by the American Association of Cereal Chemists Inc.) Therefore, the total amount of gluten protein in a flour, the protein quantity, is also important and also the protein quality thereof.

In fact, different types of wheats, in addition to their use for bread production, are the raw materials for an enormous diversity of products e.g a huge variety of pasta products, noodles, cakes, biscuits and wafers. Also, for these types of products both the protein or gluten quality and the protein quantity are important. For example durum wheats with stronger gluten quality generally give pasta with a stronger "al dente" and relatively strong gluten quality flours give cooked noodles a chewy and elastic texture. Preferences may vary between markets e.g. such that in Korea and China noodles with a chewy texture are preferred whereas in Japan a softer texture is desired.

It follows that there is a need in the wheat and wheat processing industries to provide a rapid, accurate and objective wheat quality assessment to ensure and preserve the optimal quality for a specific use and to establish a fair price for a specific consignment both in domestic and international trade.

So called rheological instruments such as the Mixograph (*National Manufacturing, Lincoln, Nebr., USA*), the Farinograph (*Brabender GmbH, Duisburg, Germany*) or the Alveograph (*Chopin Technologies, Villeneuve-la-Garenne, Cedex, France*) have long been used in the flour milling industry to monitor flour quality, especially in relation to breadmaking. (*Tronsmo et al, Cereal Chem.* 80(5):575-586). These instruments are empirical, introduced already in the 1930's and typically used on flour which means that when testing wheat, the wheat sample first needs to be milled to a flour.

Furthermore, the testing time in the equipment is long and instruments are also laborious in terms of cleaning between tests.

In practice this means that only a few tests per day can be carried out. Because of their empirical nature results are not expressed in fundamental scientific units but are manufacturer specific and expressed in e.g. Brabender units, which often are unique for the specific instrument used. This makes standardization of the instruments difficult and may lead to discrepancies between results from different users of the same type of equipment.

Fundamental rheological measurements were introduced on dough also as early as 1932 (Schofield and Scott Blair). Fundamental rheological instrumentation is designed to measure viscoelastic behavior in scientific units and also so that viscous and elastic components of the material under test can be separated. For example (Faubion and Hoseney, 1990) described dynamic oscillatory measurements applied to dough systems. Stress relaxation techniques applied to flour doughs were described by for example (Launey and Bure, 1974) and creep recovery techniques on flour doughs by for example (Bloksma and Bushuk 1988). Fundamental techniques have thus been well used in the research community but have not been adopted in the wheat industry. The main reasons are that fundamental rheological research equipment is very expensive, designed for a research lab environment, complex to use, requires technical personnel and the measurement times are very long. The instrumentation itself is not specifically designed and adapted for wheat quality measurements but of general design for a variety of materials.

For the purpose of grading and segregating wheat in order to provide a consistent quality of wheat for industrial processing and to determine a fair price to the supplier or trader of wheat, it is necessary to rapidly and with acceptable accuracy determine the quality of wheat. Specifically, there is a need to supply a consistent quality of wheat, or of products produced from wheat and to determine the quality of wheat because different end use purposes or market preferences demand different quality characteristics for optimal manufacturing performance or customer or consumer acceptance.

It follows that there is still a need in the wheat and wheat processing industries to provide a rapid, accurate and objective wheat quality assessment based on a fundamental technique that can be adopted in an industrial environment in a flour mill or at a wheat receival site and used by non technical personnel. Specifically, such rapid assessment will also help blending wheat or flour streams in an informed manner to a desired end product. It will help map production lines and precisely help controlling end use quality avoiding e.g. production waste and plant downtime, thereby corresponding to real functional and industrial needs.

The objective of the present invention is to fulfill these needs.

SUMMARY OF THE INVENTION

This objective is obtained by a method of measuring viscous and elastic properties of a gluten-containing substance including the steps of; bringing the gluten-containing substance e.g. wheat, into a powder e.g. a whole meal or flour, adding a predetermined amount of aqueous liquid e.g. saline water, to a predetermined amount of said powder, kneading said powder and liquid to a dough—i.e. adding kinetic energy to obtain a dough and to develop the viscoelastic character of the gluten in the dough—and extracting viscoelastic gluten from the dough by rinsing with said liquid, characterised by the further steps of;

shaping said gluten to a predetermined shape, placing the shaped gluten between two planar surfaces being parallel to each other, moving the planar surfaces towards each other at a controlled rate, until a maximum compression force or a minimum spacing is reached during a predetermined period of time or to a predetermined minimal distance between said planar surfaces is reached, thereby compressing the gluten placed between said planar surfaces, releasing the force on said planar surfaces so that these can move away from each other due to elastic recovery of the compressed gluten, measuring the distance between said planar surfaces during said compression and elastic recovery of the gluten, and storing the measured values.

In a preferred embodiment the actual force applied is measured and the force on the planar surfaces is maintained during said predetermined period of time also when said minimal distance between said planar surfaces is reached before the end of said predetermined period of time.

The gluten extracted from the dough is shaped to a predetermined shape, and the shaping is made in a shaping device in which the gluten is left during a predetermined holding time.

Said maximum compression force should be higher than 5 N, preferably higher than 8 N, and is preferably about 9.8 N, and said minimal distance between said planar surfaces should be 2 mm at the most, preferably 1 mm. The predetermined period of time during which said force is applied is preferably less than 60 seconds, preferably less than 45 seconds. The distance between said planar surfaces when said force is first applied, i.e. a distance corresponding to the height of the shaped gluten, is at least ten times said minimal distance between said planar surface.

The invention also relates to an apparatus for measuring viscous and elastic properties of a gluten-containing substance including means for kneading a mixture of a predetermined amount of gluten-containing powder and a predetermined amount of water to a dough and extracting gluten from the dough, characterised by means for shaping said extracted gluten, and further characterised in that it includes two parallel planar plates and means for moving said plates towards each other at a controlled rate, until a maximum compression force or a minimum spacing is reached, means for releasing said plates from said compression force after a predetermined period of time, means for maintaining a predetermined minimal distance between said planar surfaces, means for measuring the distance between said planar plates, and means for storing the measured values and means for retrieving stored measures.

In a preferred embodiment, a balanced parallel-arms mechanism maintains parallel alignment between said plates, said mechanism being connected to a spiral spring via an arm transferring the constant force given by the spiral spring to said mechanism and where the apparatus includes a drive motor for winding said spiral spring to give a desired force and for rewinding said spring.

BRIEF DESCRIPTION OF THE DRAWINGS

The invention will now be described with reference to the enclosed figures, of which.

DESCRIPTION OF EMBODIMENTS

In FIGS. 1-4, a perspective view of an apparatus 1 for measuring viscous and elastic properties of a gluten-containing substance is schematically shown. This apparatus includes two compression plates 2 and 3, respectively, between which a sample of the gluten-containing substance to be tested is placed after being worked to a viscoelastic gluten in a per se known manner.

Figure 1:
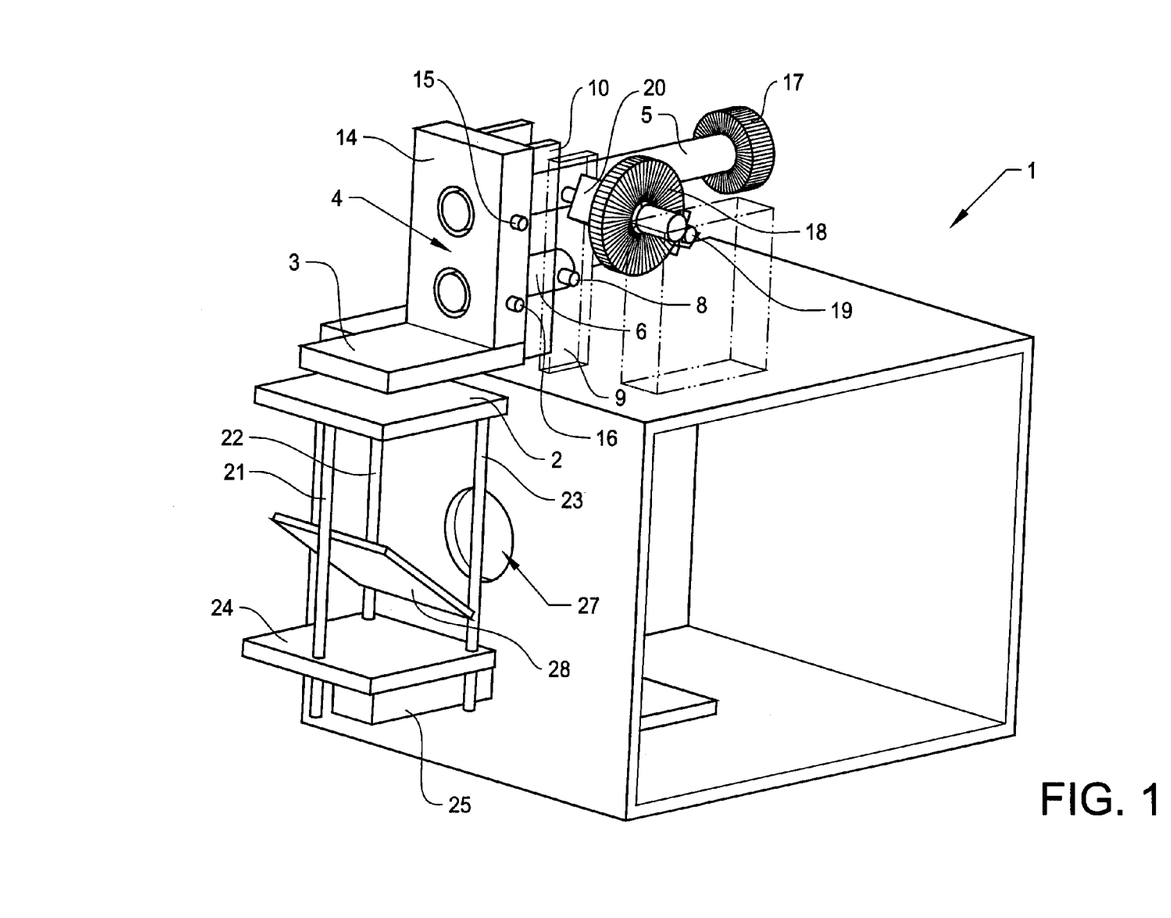
FIG. 1 schematically shows a perspective view of a apparatus for measuring viscous and elastic properties of a gluten-containing substance according to a preferred embodiment of the invention, the perspective view showing the right side of the apparatus.
Figure 2:
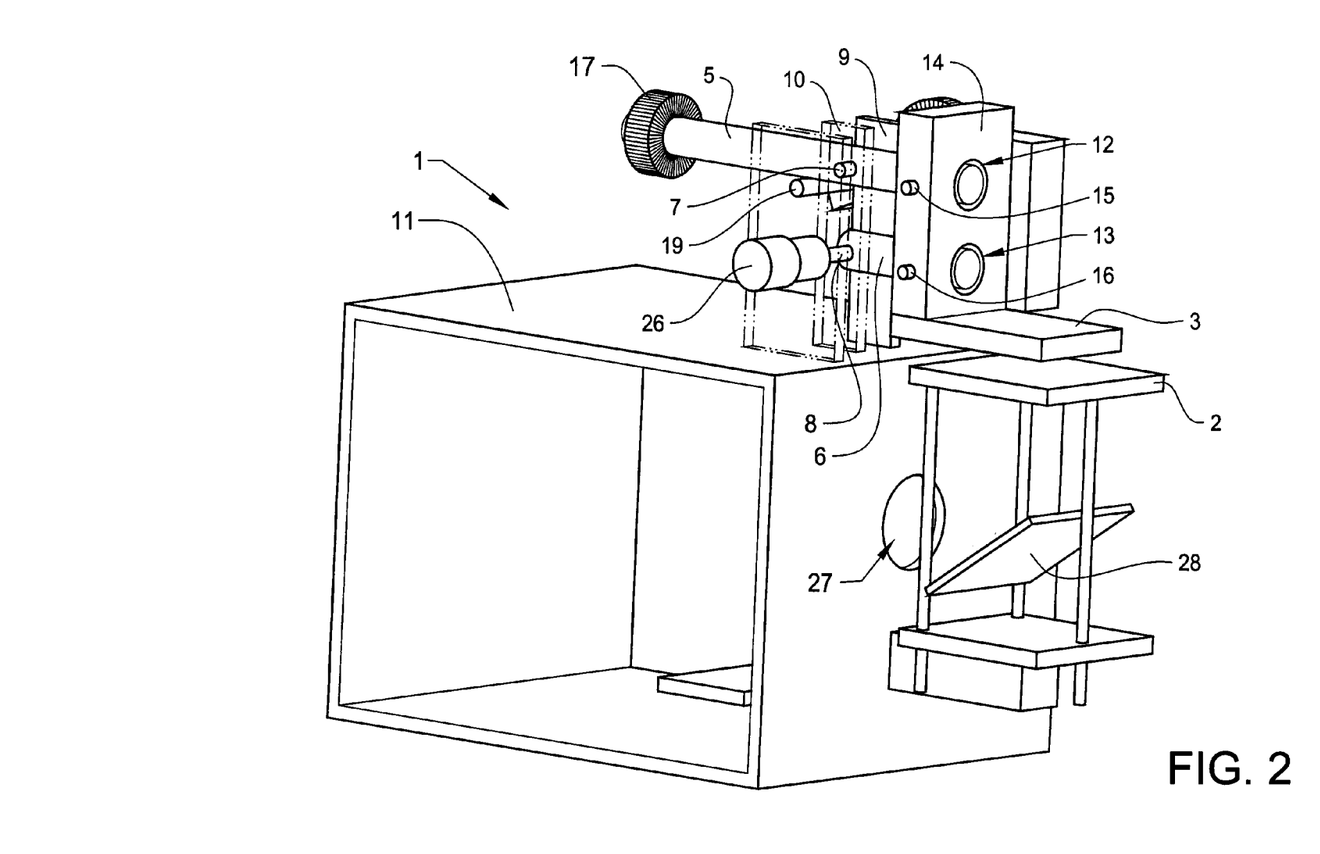
FIG. 2 shows a similar perspective view of the apparatus in FIG. 1, showing the left side thereof.
Figure 3:
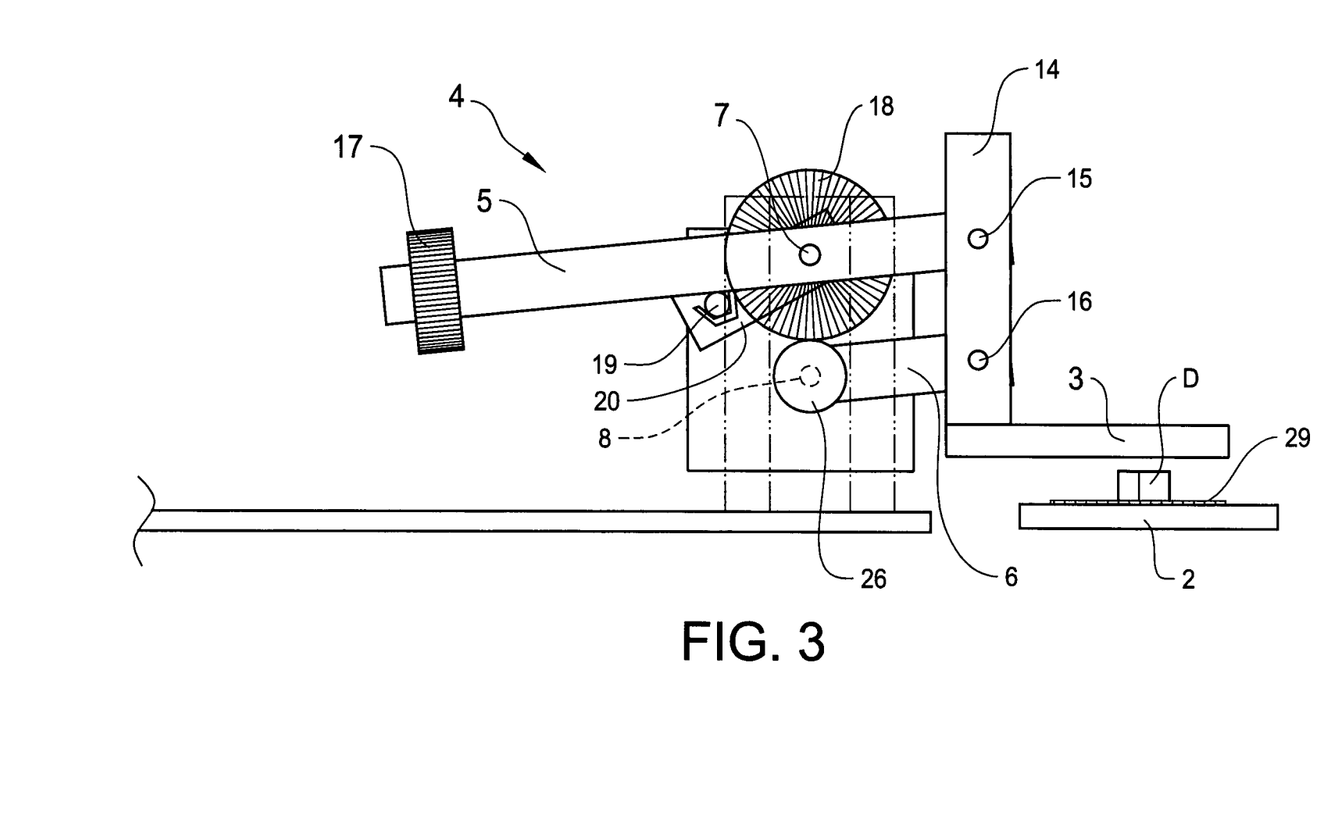
FIG. 3 shows a side view of the parallel-arms mechanism and the two compression plates of the apparatus in FIGS. 1 and 2 with the compression plates spaced from each other and in a relaxed state.

The upper compression plate 3 is held by a parallel-arms mechanism 4 which maintains parallel alignment between the compression plates throughout a range of motion, for example 0-15 mm spacing. This mechanism includes two parallel arms 5 and 6 which are pivotally supported on pins 7,8 supported in brackets 9,10 upstanding from upper wall of house 11 of the apparatus. The arms 5,6 extend beyond the front side of the housing 11 and through openings 12,13 in a holder 14, to which holder the upper compression plate 3 is attached. The arms are pivotally held in these openings 12,13 by pins 15,16. The distance between pins 15 and 16 is the same as between pins 7 and 8 as well as the distances between pins 7 and 15 are the same as between 8 and 16, respectively. In FIG. 3 the parallel-arms mechanism is shown in an upper position, in which a gluten D of a gluten-containing substance can be placed between the upper compression plate 3 and the lower compression plate 2, and in FIG. 4 the parallel-arms mechanism is shown in a lower position, in which the gluten D is compressed between plates 2 and 3.

Figure 4:
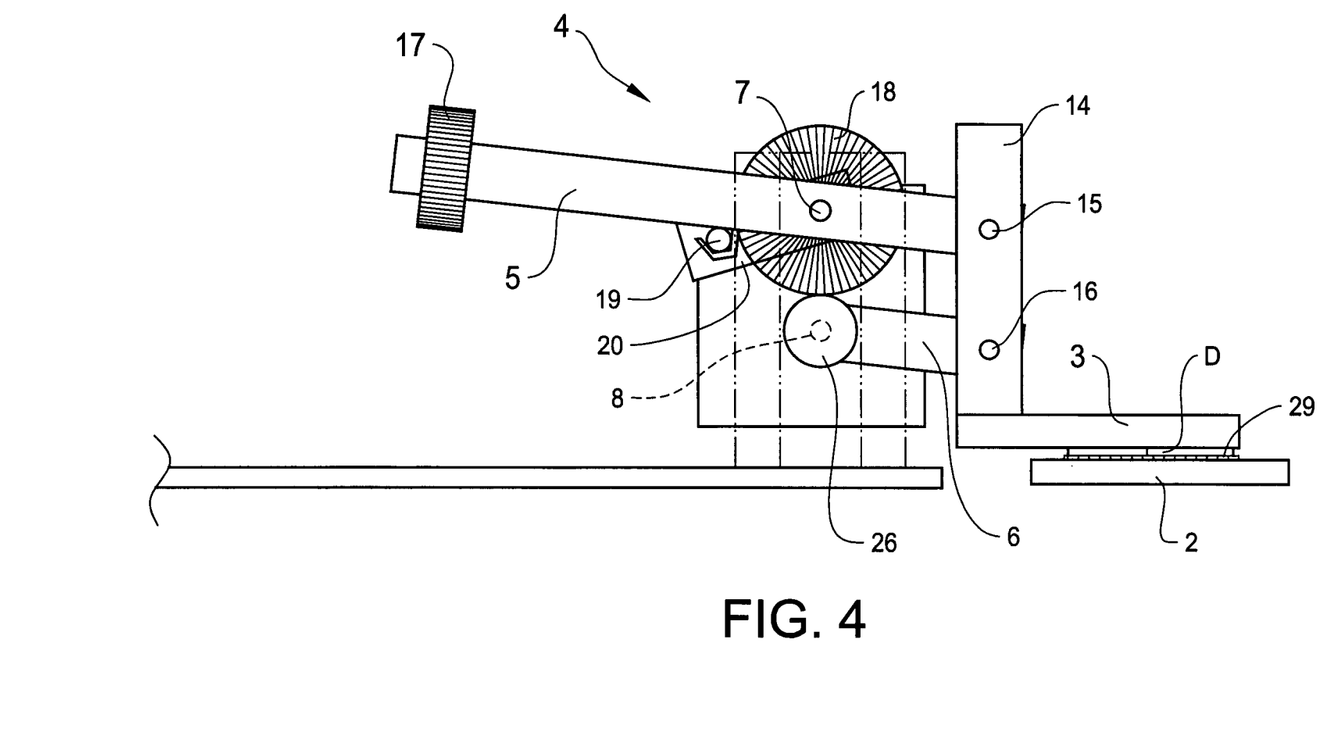
FIG. 4 shows a similar side view as FIG. 3 with the compression plates urged towards each other, FIG. 5 schematically shows the shaping of a gluten sample to a sample body for use in the apparatus according to FIGS. 1-4.

The parallel-arms mechanism 4 is balanced by a counterweight 17 so that the compression plate 3 will stay in its position without inflict any load on the gluten D when the load acting on the parallel-arms mechanism to compress the gluten D as illustrated in FIG. 4, is released. This is important for enabling a measurement of the extent of elastic recovery thereby separating the viscous and elastic properties of the gluten D by monitoring the position of the compression plate 3. The counterweight 17 is located at the end of a prolongation of arm 5 of the parallel-arms mechanism.

For loading the parallel-arms mechanism 4 a spiral spring 18 of the type which applies a consistent, specified force on the mechanism 4 during compression of a gluten between plates 2,3 is used. The spiral spring 18 can for example be a spiral spring with the trade name 2751, from All-rite Spring Company, USA. A drive motor (shown as outline in the figures for the sake of clarity) is used to load the spiral spring to a desired force and to unload it. The drive motor can for example be a motor with the trade name 2L008 from W.W Graiger Inc., USA.

The outer end of the spiral spring 18 is coupled to an end of a transfer arm 19. This transfer arm is held in a holder 20 which can swing around an axis coincident with the pin 7. When the spiral spring 18 is loaded by the motor, the transfer arm 19 will swing upward thereby acting on the prolonged upper arm 5 of the parallel-arms mechanism 4 at a distance from its pivotal connection to pin 7. Thereby the force of the spiral spring 18 will be transferred to the parallel-arms mechanism and consequently to the compression plates 2,3.

The lower compression plate 2 is adjustably supported on three rods 21-23 which in turn is supported by a plate 24. The plate 24 acts on a load cell 25, for example a load cell with the trade name Model 1022 from Vishay Intertechnology Inc., USA, measuring the compression force acting on the compression plates.

A high-resolution rotation sensor 26, for example a sensor with the trade name MAB25A from Megatron AG, Germany, measures the rotation of the lower arm 6 of the parallel-arms mechanism 4 around pin 8. The position of the upper compression plate 3 relative to plate 2 can then easily be calculated based on the measured angle of rotation of arm 6.

A rotation sensor can optionally be used for measuring the position of the shaft of the motor for loading and unloading the spiral spring in order to predict spring force.

The compression plates 2,3 are preferably of a transparent material to permit unobstructed view of a gluten placed therebetween. In such a case a camera can be placed within the housing 11 for recording images of the gluten during compressing and relaxation thereof. A hole 27 is made in the front wall of the housing 11 and a mirror 28 is located beneath compression plate 2 in order to facilitate such recording.

A data processing unit or a computer (not shown) is disposed within the housing 11 and is connected to the drive motor and all sensors and the optional camera. In this unit all measured values are stored and the unit also contains software for controlling the measuring and compressing procedure. The calculations of the position of the upper compression plate 3 can be made in this unit but it is possible to connect this unit to an external PC for calculations and display of diagrams showing the compression of the gluten and its elastic recovery.

Before the measurements can be done in the apparatus described above, the gluten-containing substance to be tested is brought to a powder or flour by crushing or milling (unless already in powder form). Thereafter a fixed amount of 2% saline solution is added to a fixed amount of the powder and this mixture is kneaded to a dough which thereafter is extracted to a viscoelastic gluten sample by rinsing with saline solution. Preferably this is done with the aid of a special instrument having the trade name Glutomatic from Perten Instruments AB, Huddinge, Sweden, in which a mixture of 10 mg of gluten-containing powder and approximately 4.8 ml of saline solution is first kneaded to a dough and thereafter viscoelastic gluten is extracted through rinsing with saline solution.

Figure 5:
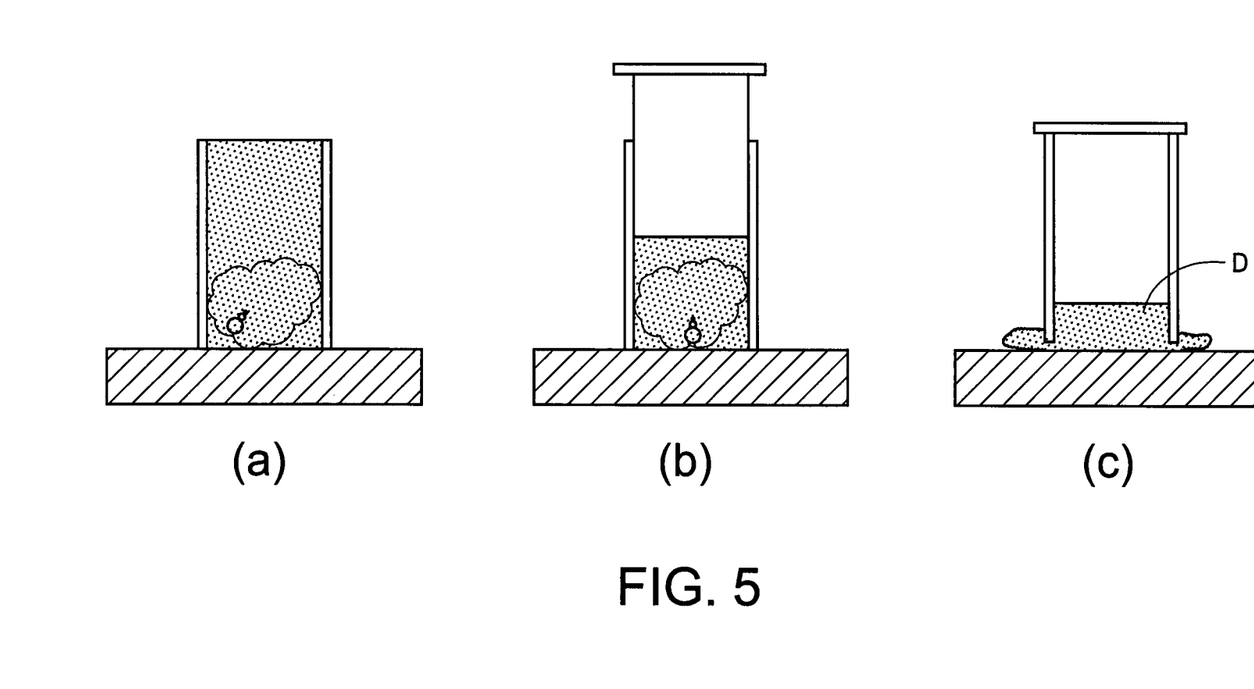

Thereafter, the sample is formed to a predetermined shape. In the shown embodiment a cylindrical shape has been chosen for the sample but other shapes, such as a cubic or a parallelepipedic shape, can be chosen. The shaping of a cylindrical sample is schematically shown in FIG. 5. As can be seen from this figure the sample is placed into an open cylinder standing on a planar substrate (FIG. 5a). Thereafter, a piston is inserted into the open end of the cylinder (FIG. 5b) and this piston is pressed down until it reaches an end position determined by a flange standing out from the upper end of the piston abutting the upper edge of the cylinder (FIG. 5c). The chosen height of this cylindrical sample is 10 mm and its diameter is 15 mm. The pressing down of the piston until the flange touches the cylinder results in a constant volume sample as the excess is forced out under the bottom cylinder edge. A rotary motion of the cylinder will then cut the excess gluten free from the retained sample.

The shaped cylindrical sample is then held within the cylinder with the piston in the end position shown in FIG. 5c for a determined period of time. In the described embodiment a period of 5 minutes is used. By this holding of the cylindrical shape of the sample, the sample is caused to "remember" its cylindrical shape due to the plastic component of viscosity of the sample.

Thereafter, possible surplus of gluten that has leaked out of the cylinder, see FIG. 5c, is removed and the gluten D is then pressed out of the cylinder by a suitable tool and thereafter placed on compression plate 2 of the apparatus 1.

Then the compression plate 3 is moved to abut the planar top of the cylindrically shaped gluten D.

The compression procedure is then started by actuation of apparatus 1, for example by pushing a "Run" button. The motor then runs in a direction to wind the spiral spring 18 which in turn results in the transfer arm 19 acting on the upper arm 5 of the parallel-arms mechanism 4 thereby swinging the upper arm 5 in a clockwise direction around pin 7. This results in a downward movement of compression plate 3, which presses against the gluten with a force having a constant relationship to the force of the spiral spring 18. The force acting on the gluten D and the lower compression plate 2 is measured by the load cell 25 and when a predetermined or prescribed force is reached the motor winding the spiral spring stops. The predetermined force acting on the gluten D can be freely chosen but should be preferably be higher than 5 N, more preferably higher than 8 N, and most preferably about 9.8 N. A force of 9.8 N has been proven to be suitable for testing viscoelastic properties of gluten-containing substances produced from powder of wheat.

The predetermined compression force acting on the gluten D is maintained during a pre-determined compression period of time. This compression period should be short in order to enable the measurement procedure to be rapid and industrially applicable. The compression period is therefore chosen to be less than 60 seconds, preferably less than 45 seconds, and most preferably 30 seconds. Due to the compression force acting on the gluten D, the gluten D deforms and the distance between the compression plates 2,3 decreases. If the gluten D is viscous or weakly elastic enough to reduce the compression force, as measured by the load cell, the motor is again activated for a short interval until the predetermined force again is reached. By monitoring the force measured by load cell 25, the apparatus controller will pulse the drive to the motor as required to maintain the predetermined compression force during the compression period.

Directly after the end of the compression period, the motor is activated in a direction to rapidly unwind the spiral spring 18 and to remove the transfer arm 19 from contact with the upper arm 5 of the parallel-arms mechanism 4. The compression plate 3 is then free to move upward.

Due to the balancing of the parallel-arms mechanism 4, the compression plate will remain in place in contact with the top of the gluten D also after removal of the compression force. When the gluten D in accordance with its viscoelastic properties strive to recover its initial cylindrical shape and thereby recover a certain degree of its initial height, the compression plate 3 will follow the upward movement of the top of the gluten. The degree to which the gluten D can retain its initial height, i.e. the height of the cylinder when placed in the apparatus 1 and before compression thereof, is dependent on the gluten quality, i.e. the viscoelastic properties, of the gluten-containing substance from which the gluten D is made. In order to measure this recovery in height, the movement of the compression plate is measured during a predetermined period of time. A suitable time interval is 15-60 seconds, preferably 30 seconds.

The motor position, load cell force reading, and sensor readings are recorded at regular data acquisition intervals, e.g. every 100 milliseconds, and stored in the data processing unit.

In order to prevent over-stretching of gluten-containing substances comprising weak gluten, a shim 29 of a certain height, 2 mm at the most and preferably 1 mm, can be placed on the lower compression plate 2 before the gluten is placed thereon. This shim is preferably circular and has a dimension so that the cylindrical gluten can be compressed and deformed in a radial direction without contacting this shim.

Figure 6:
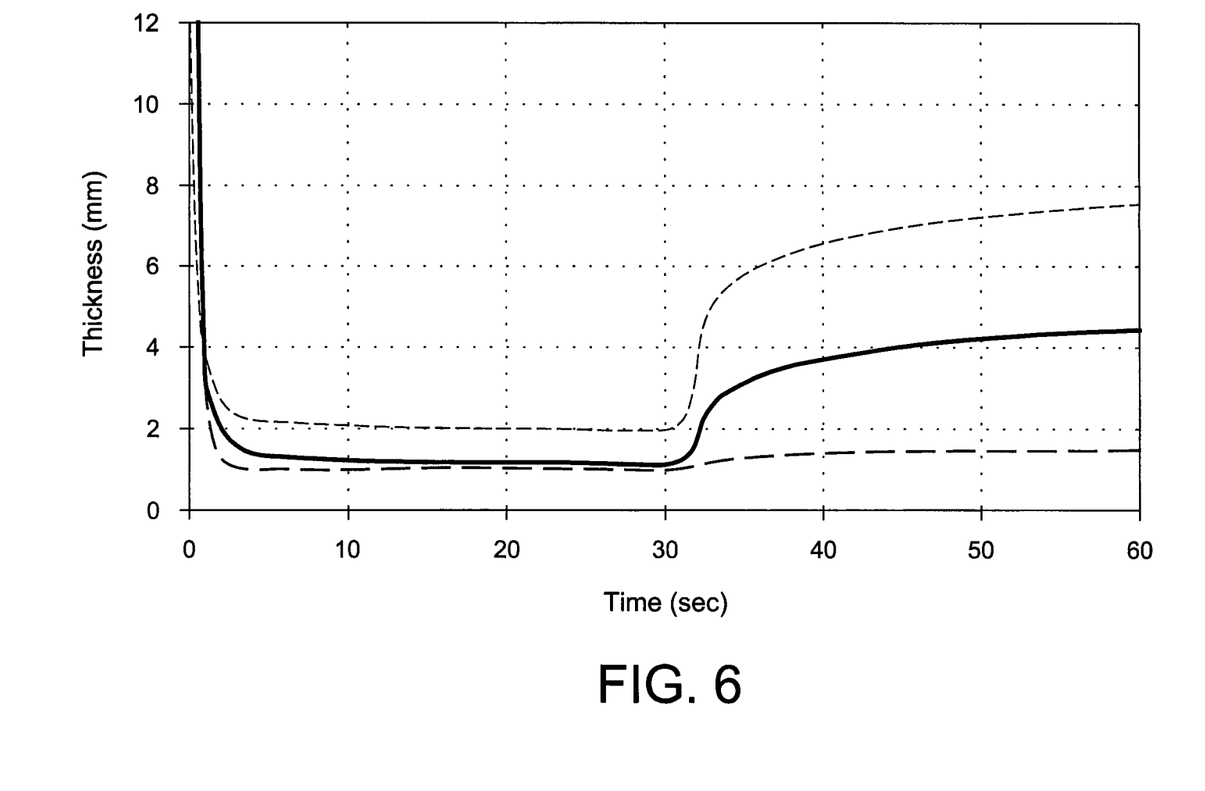
FIG. 6 shows a diagram of the compression and recovery of different glutens made from extracting doughs of different types of wheat.

FIG. 6 shows a diagram of the distance between the compression plates 2 and 3 as a function of time in tests of several types of wheat by the method described and in the apparatus 1 according to the invention.

Each of the three recovery profile curves has at least for principal regions. For example there is a) a rapid deformation within the first few seconds after the initial compression and b) a slow continued deformation during the entire compression cycle and occurring just after the first rapid deformation. Furthermore, there is c) a rapid initial recovery as the force is released and d) a slow continued recovery until the test is interrupted. The first two stages a,b provide information on the viscous properties and the last two stages c,d on the elastic properties of the glutens.

As is evident from the curves or recovery profiles in FIG. 6, the viscoelastic properties of the glutens are different for the different wheat types. Since the test procedure is automatic and performed in the same manner, the results are only depending on the properties of the different glutens. If curves for wheat types having known desired properties are made by the method described above using the apparatus according to the invention such curves can be used as reference curves for determining the quality of the wheat from the aspect of viscoelastic properties of the tested gluten. The method and apparatus according to the present invention thus provides a rapid and accurate test of the functional quality of wheat which can be used in a flour mill or at a wheat receival site. Furthermore, the method does not require any particular education or skill to be performed and can thus be used by non skilled personnel.

The embodiment described can be modified in several aspects without leaving the scope of invention. The parallel movement of the upper compression plate can for example be accomplished in other ways than by a parallel-arms mechanism, for example the lower arm 6 can be deleted and the movement of the holder of the compression plate 3 can be guided in guides or the like allowing only vertical movement thereof. Furthermore, the compression plates can be coated by a thin coat of e.g. canola oil before the cylindrical gluten is placed thereon in order to ensure that the gluten does not stick to the plates. Means for preparation, such as crushing, the gluten-containing substance and kneading a dough thereof, rinsing and preparing viscoelastic gluten from the dough as well as manual or automatic means for shaping the gluten to a cylindrical shape can be integrated with the apparatus 1. The method and apparatus can be used for testing the viscoelastic properties of a dough without preparing a gluten, also on a sample prepared directly from isolated vital gluten as well of other substances than wheat, meal or flour, e.g. corn gluten, cheese products and synthetic polymer products, such as earplugs. The scope of invention shall therefore only be limited by the content of the enclosed patent claims.

The invention claimed is:

1. A method of measuring viscous and elastic properties of a gluten-containing substance comprising the steps of:
   bringing the gluten-containing substance into a powder;
   adding a predetermined amount of aqueous liquid to a predetermined amount of said powder;
   kneading said powder and liquid to a dough; and
   extracting viscoelastic gluten from the dough by rinsing with said liquid;
   shaping said gluten to a predetermined shape;
   placing the shaped gluten (D) between two planar surfaces (2,3) being parallel to each other;
   moving the planar surfaces (2,3) towards each other during a predetermined period of time and at a controlled rate until a maximum compression force or minimum spacing is reached, thereby compressing the gluten placed between said planar surfaces;
   releasing the force on said planar surfaces so that these can move away from each other due to elastic recovery of the compressed gluten (D);
   measuring the distance between said planar surfaces (2,3) during said compression and elastic recovery of the gluten; and
   storing the measured values.

2. The method according to claim 1, wherein the actual force applied is measured.

3. The method according to claim 1, wherein said planar surfaces (2,3) are prevented from moving closer to each other when a predetermined minimal distance between said planar surfaces is reached.

4. The method according to claim 3, wherein said minimal distance between said planar surfaces is 2 mm at the most.

5. The method according to claim 1, wherein the force on the planar surfaces (2,3) is maintained during said predetermined period of time also when said minimal distance between said planar surfaces is reached before the end of said predetermined period of time.

6. The method according to claim 1, wherein the gluten (D) is shaped to a predetermined shape and that said shape is maintained for a period of time before the gluten (D) is placed between said planar surfaces in order to establish within the gluten a preferred arrangement of this shape.

7. The method according to claim 1, wherein the shaping of the gluten is made in a shaping device in which a constant volume portion of the gluten is shaped and in which the shaped gluten is left during a predetermined holding time.

8. The method according to claim 1, wherein said compression force is higher than 5 N.

9. The method according to claim 1, wherein the predetermined period of time during which said compression force is applied is less than 60 seconds.

10. The method according to claim 1, wherein the distance between said planar surfaces (2,3) when the compression force is first applied, the a distance corresponding to the height of the shaped gluten (D), is at least ten times said minimal distance between said planar surface.

11. An apparatus for measuring viscous and elastic properties of a gluten-containing substance including means for kneading a mixture of a predetermined amount of gluten-containing powder and a predetermined amount of aqueous liquid to a dough and extracting gluten from the dough by rinsing, characterised by means for shaping said gluten, and further characterised in that it includes two parallel planar plates (2,3) and means (4,18,19,20) for moving said plates (2,3) towards each other at a controlled rate, until a maximum compression force or a minimum spacing is reached, means for releasing said plates (2,3) from said constant force after a predetermined period of time, means (26) for measuring the distance between said planar plates (2,3), and means for storing the measured values and means for retrieving stored measures.

12. The apparatus according to claim 11, wherein a balanced parallel-arms mechanism (4) maintain parallel alignment between said plates (2,3), said mechanism being connected to a spiral spring (18) via an arm (19) transferring the constant force given by the spiral spring (18) to said mechanism.

13. The apparatus according to claim 12, wherein the apparatus includes a drive motor for winding said spiral spring (18) to give a desired force and for unwinding said spring.

14. The apparatus according to claim 10, including means (28) for maintaining a predetermined minimal distance between said planar surfaces (2,3).

15. The method according to claim 2 wherein the force on the planar surfaces (2,3) is maintained during said predetermined period of time also when said minimal distance between said planar surfaces is reached before the end of said predetermined period of time.

16. The method according to claim 3 wherein the force on the planar surfaces (2,3) is maintained during said predetermined period of time also when said minimal distance between said planar surfaces is reached before the end of said predetermined period of time.

17. The method according to claim 4 wherein the force on the planar surfaces (2,3) is maintained during said predetermined period of time also when said minimal distance between said planar surfaces is reached before the end of said predetermined period of time.

18. The apparatus according to claim 11, including means (28) for maintaining a predetermined minimal distance between said planar surfaces (2,3).

19. The apparatus according to claim 12, including means (28) for maintaining a predetermined minimal distance between said planar surfaces (2,3).

20. The apparatus according to claim 13, including means (28) for maintaining a predetermined minimal distance between said planar surfaces (2,3).

\* \* \* \* \*